(12) United States Patent
Sabb et al.

(10) Patent No.: US 7,271,164 B2
(45) Date of Patent: Sep. 18, 2007

(54) CYCLOHEPTA[B][1,4]DIAZEPINO [6,7,1,-HI]INDOLES AND DERIVATIVES

(75) Inventors: Annmarie L. Sabb, Pennington, NJ (US); Robert L. Vogel, Collingswood, NJ (US)

(73) Assignee: Wyeth, Madison, NJ (US)

( * ) Notice: Subject to any disclaimer, the term of this patent is extended or adjusted under 35 U.S.C. 154(b) by 167 days.

(21) Appl. No.: 10/966,227

(22) Filed: Oct. 15, 2004

(65) Prior Publication Data

US 2005/0054635 A1   Mar. 10, 2005

Related U.S. Application Data

(63) Continuation of application No. 10/016,743, filed on Nov. 2, 2001, now Pat. No. 6,858,604.

(60) Provisional application No. 60/245,598, filed on Nov. 3, 2000.

(51) Int. Cl.
  *A61K 31/55* (2006.01)
  *A61P 25/00* (2006.01)
  *A61P 25/24* (2006.01)
  *C07D 243/00* (2006.01)

(52) U.S. Cl. .................................... 514/219; 540/555

(58) Field of Classification Search ............... 514/219; 540/555
See application file for complete search history.

(56) References Cited

U.S. PATENT DOCUMENTS

| | | | |
|---|---|---|---|
| 3,235,564 A | 2/1966 | Wagner | 549/11 |
| 3,296,252 A | 1/1967 | Frey et al. | 540/493 |
| 3,329,676 A | 7/1967 | Bell et al. | 540/493 |
| 3,335,134 A | 8/1967 | Frey et al. | 540/493 |
| 3,417,101 A | 12/1968 | Bell et al. | 549/27 |
| 3,466,274 A | 9/1969 | DeRidder | 540/556 |
| 3,714,149 A | 1/1973 | Hepter | 540/496 |
| 3,914,250 A | 10/1975 | Kim | 260/315 |
| 4,997,831 A | 3/1991 | Bays et al. | 514/211.1 |
| 5,045,545 A | 9/1991 | Bays et al. | 514/284 |
| 5,834,454 A | 11/1998 | Kitano et al. | 514/183 |
| 6,503,900 B2 | 1/2003 | Sabb et al. | 514/219 |
| 6,699,852 B2 | 3/2004 | Robichaud et al. | 514/183 |
| 6,720,316 B2 | 4/2004 | McWhorter, Jr. | 514/215 |
| 6,759,405 B2 | 7/2004 | Sabb et al. | 514/219 |
| 6,777,402 B2 | 8/2004 | Nifantiev et al. | 514/183 |
| 6,777,407 B2 | 8/2004 | Sabb et al. | 514/219 |
| 6,858,604 B2 * | 2/2005 | Sabb et al. | 514/219 |
| 2002/0086860 A1 | 7/2002 | Sabb et al. | 514/220 |
| 2002/0107242 A1 | 8/2002 | Sabb et al. | 514/219 |
| 2002/0119966 A1 | 8/2002 | Sabb et al. | 514/219 |
| 2002/0173503 A1 | 11/2002 | Robichaud et al. | 514/211.1 |
| 2003/0050300 A1 | 3/2003 | McWhorter Jr. | 514/211.1 |

FOREIGN PATENT DOCUMENTS

| | | |
|---|---|---|
| EP | 0344015 A2 | 11/1989 |
| EP | 0357417 A1 | 3/1990 |
| JP | 10-237073 | 9/1998 |
| SU | 930902 | 11/1982 |
| WO | WO90/15058 A1 | 12/1990 |
| WO | WO96/29316 A1 | 9/1996 |
| WO | WO97/30999 A1 | 8/1997 |
| WO | WO97/31000 A1 | 8/1997 |
| WO | WO99/66934 A1 | 12/1999 |
| WO | WO99/67219 A1 | 12/1999 |
| WO | WO 00/35922 A1 | 6/2000 |
| WO | WO 00/64899 A1 | 11/2000 |
| WO | WO 00/77002 A1 | 12/2000 |
| WO | WO 01/12603 A1 | 2/2001 |
| WO | WO 02/08186 A2 | 1/2002 |

(Continued)

OTHER PUBLICATIONS

S. Archer et al., J. Am. Chem. Soc., 79, 5783-5785 (1957).

(Continued)

*Primary Examiner*—Brenda Coleman
(74) *Attorney, Agent, or Firm*—Fitzpatrick, Cella, Harper & Scinto

(57) ABSTRACT

This invention provides compounds of the formula:

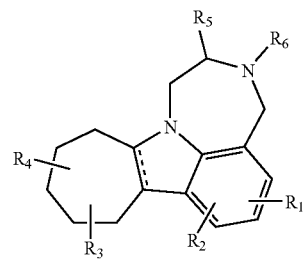

wherein $R_1$ and $R_2$ are each, independently, H, alkyl, cycloalkyl, —$CH_2$-cycloalkyl, alkoxy, halogen, fluorinated alkyl, —CN, —NH—$SO_2$-alkyl, —$SO_2$—NH-alkyl, alkyl amide, amino, alkylamino, dialkylamino, fluorinated alkoxy, acyl, or phenoyl or thiophenoyl; $R_3$ and $R_4$ are each, independently, H, alkyl or cycloalkyl; $R_5$ is H or alkyl; $R_6$ is H or; and the dashed line indicates an optional double bond; or a pharmaceutically acceptable salt thereof, and pharmaceutical compositions and methods utilizing these compounds for the treatment or prevention of disorders including obsessive-compulsive disorder, depression, anxiety, generalized anxiety disorder, schizophrenia, migraine, sleep disorders, eating disorders, obesity, epilepsy, and spinal cord injury.

16 Claims, No Drawings

FOREIGN PATENT DOCUMENTS

| WO | WO 02/36596 A2 | 5/2002 |
| WO | WO 02/42304 A2 | 5/2002 |
| WO | WO 02/059124 A2 | 8/2002 |
| WO | WO 02/059129 A2 | 8/2002 |

OTHER PUBLICATIONS

L. Zhang et al., Tetrahedron Letters, 36(46), 8387-8390 (1995).
G.E. Stokker, Tetrahedron Letters, 37(31), 5453-5456 (1996).
Cuadro et al., Synthetic Communications, 21(4), 535-544 (1991).
W. Perkin et al., J. Chem. Soc., 123, 3242-3247 (1923).
H. Booth et al., J. Chem. Soc., 158, 2302-2311 (1958)
Gregory R. Martin et al., J. Med. Chem., 32, 1052-1056 (1989).
J.L. Browning et al., Society for Neuroscience Abstracts, Oct. 1999, 2075, 25(2), Abstract 830.12.
Jackson B. Hester et al., J. Med. Chem., 13, 827-835 (1970).
Dong H. Kim, J. Heterocycl. Chem., 13(6), 1187-92 (1976).
H.P. Harter et al., Chimia, 30, 50-52 (1976).
P.J. Cowen et al., Nature 376, 557 (Aug. 1995).
A.J. Robichaud et al., Annual Reports in Medicinal Chemistry, 35, 11-20 (2000).
D. Hoyer et al., Pharmacology & Experimental Therapeutics 46(2), 157-203 (1994).
L. Tecott et al., Nature, 374, 542-546 (Apr. 1995).
D.H. Kim, J. Heterocycl. Chem., 12, 1323-1324 (Dec. 1975).
M.J. Bishop et al., Expert Opin. Ther. Patents, 13(11), 1691-1705 (2003).
Shunji Naruto et al., Tetrahedron Letters, 39, 3399-3402 (1975).
A.N. Grinev et al., Chem. Heterocycl. Compd., 19(9), 959-961 (1983).
A.N. Grinev et al., Chem. Heterocycl. Compd., 19(12), 1312-1315 (1983).
E.V. Lamanova et al., Pharm. Chem., J., 23(2), 113-115 (1989).
D.H. Kim et al., Journal of Medicinal Chemistry, 20(2), 209-212 (1977).
L. Toscano et al., J. Heterocyclic Chem., 13, 475-480 (1976).
A. Katritzky et al., Synthesis, 10, 1487-1490 (1998).
F. Gatta et al., Edizione Scientifica, 30(8), 631-641 (1975).
W. Lopes et al., Journal of Brazilian Chemical Society, 4(1), 34-39 (1993).

* cited by examiner

CYCLOHEPTA[B][1,4]DIAZEPINO[6,7,1,-HI]INDOLES AND DERIVATIVES

This application is a continuation of application Ser. No. 10/016,743, filed Nov. 2, 2001, now U.S. Pat. No. 6,858,604 which claims the benefit under 35 U.S.C. §119(e) of provisional Application No. 60/245,598, filed Nov. 3, 2000, the entire disclosure of which is hereby incorporated by reference.

The present invention relates to cyclohepta[b][1,4]diazepino[6,7,1-hi]indoles and derivatives thereof, which are serotonin 5-hydroxytryptamine $2_C$ ($5HT_{2C}$) receptor agonists useful for the treatment or prevention of disorders including obsessive-compulsive disorder, depression, anxiety, generalized anxiety disorder, schizophrenia, migraine, sleep disorders, eating disorders, obesity, epilepsy, and spinal cord injury.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the 21$^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J.) 147-210 (Wiley-Liss, New York, 1991).] The $5HT_{2C}$ receptor (formerly called the $5HT_{1C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558-564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M. , Williams, C., Walsh, A. E. S., Fairburn, C. G. *Nature* 376: 557 (1995).] Tecott, et al have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Daliman, M. F., Jullus, D. *Nature* 374: 542-546 (1995).] Compounds of this invention are $5HT_{2C}$ receptor subtype selective agonists which are selective over other monoamine receptors, causes a reduction in food intake and result in a reduction in weight gain. Other therapeutic indications for $5HT_{2C}$ agonists are obsessive compulsive disorder, depression, panic disorder, schizophrenia, sleep disorders, eating disorders, epilepsy, and spinal cord injury.

U.S. Pat. No. 3,914,250 (Oct. 21, 1975) describes 1,4-diazepino[6,5,4-jk]carbazoles as anticonvulsant agents. The compounds of this invention are not carbazoles. This invention relates to cyclohepta[b][1,4]diazepino[6,7,1-hi]indoles and derivatives which bind to and activate $5HT_{2C}$ receptors in the CNS and are useful for the treatment of CNS disorders which can benefit from modulation of the $5HT_{2C}$ receptor.

DESCRIPTION OF THE INVENTION

This invention provides compounds of formula I having the structure

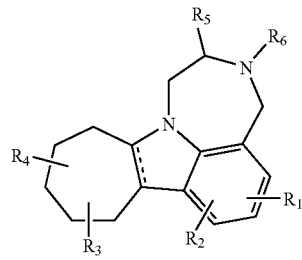

wherein:
$R_1$ and $R_2$ are each, independently, hydrogen, alkyl of 1-6 carbon atoms, cycloalkyl of 3 to 7 carbon atoms, —CH$_2$-cycloalkyl of 3 to 7 carbon atoms, alkoxy of 1-6 carbon atoms, halogen, fluorinated alkyl of 1 to 6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, or phenoyl or thiophenoyl;
$R_3$ and $R_4$ are each, independently, hydrogen, $C_1$-$C_6$ alkyl or cycloalkyl of 3 to 7 carbon atoms;
$R_5$ is hydrogen or $C_1$-$C_6$ alkyl;
$R_6$ is hydrogen or $C_1$-$C_6$ alkyl; and
wherein the dashed line indicates an optional double bond;
or a pharmaceutically acceptable salt thereof, In the definitions of $R_1$ and $R_2$ herein, the fluorinated alkyl and fluorinated alkoxy groups indicate the specified alkyl or alkoxy groups having any amount of fluorine substitution, including, but not limited to, groups such as —CHF$_2$, —CF$_3$, —C$_2$F$_5$, —OCF$_3$, etc.

One group of compounds of this invention are those having formula 1, above, in which $R_1$, $R_2$, $R_5$ and $R_6$ are each hydrogen and $R_3$ and $R_4$, are as defined above, or a pharmaceutically acceptable salt thereof. Another group of compounds of this invention are those in which $R_5$ is hydrogen and $R_1$, $R_2$, $R_3$, $R_4$ and $R_6$ are as defined above. In another group of compounds of this invention, $R_5$, $R_2$ and $R_3$ are hydrogen and $R_1$, $R_4$ and $R_6$ are as defined above.

The $5HT_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, sleep disorders, such as sleep apnea, eating disorders, such as hyperphagia, bulimia or anorexia nervosa, obesity, epilepsy, and premenstrual tension.

This invention also includes methods of utilizing the compounds herein in treatments or preventitive regimens for treatment of central nervous system deficiencies associated with trauma, stroke, neurodegenerative diseases or toxic or infective CNS disorders including, but not limited to, encephalitis or menengitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength.

The compounds of this invention contain asymmetric carbon atoms and thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The term "alkyl" includes both straight- and branched-chain saturated aliphatic hydrocarbon groups and cycloalkyl groups. Halogen is Cl, Br, F, or I.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

Preferred compounds of this invention are those in which R is hydrogen. Especially preferred are compounds, which are enantiomerically pure stereoisomers of compounds where R is hydrogen and the indole ring is reduced or not reduced.

The compounds of this invention can be prepared according to the following scheme from commercially available starting materials or starting materials, which can be prepared using literature procedures. Scheme 1 shows the preparation of a key intermediate and Scheme 2 shows the preparation of representative compounds of this invention.

Scheme I

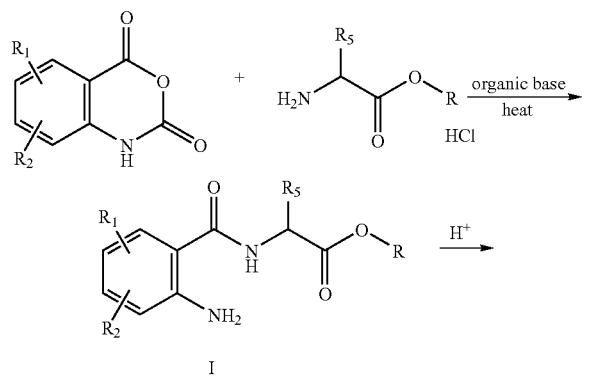

-continued

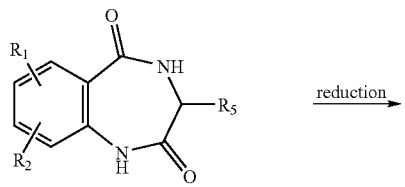

II

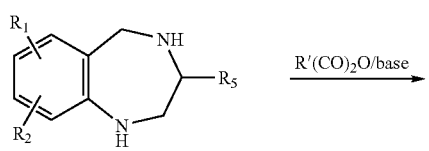

III

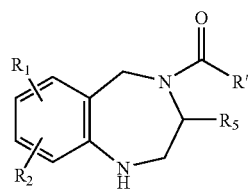

IV

According to Scheme I, a substituted or unsubstituted isatoic anhydride is allowed to react with substituted or unsubstituted glycine hydrochloride or an ester of the same in an organic base such as pyridine or triethylamine, to give either open-chain intermediate I or the benzodiazepinedione II. Intermediate I can be converted to intermediate II by heating in the presence of an acid, such as acetic acid. The benzodiazepinedione II is reduced to the benzodiazepine III using a reducing agent such as lithium aluminum hydride or a borane-tetrahydrofuran complex. The secondary nitrogen atom in III is protected using a protecting group, such as an amide by reacting III with an acylating agent, such as acetic anhydride, in the presence of a base, such as triethylamine, to give an acylated benzodiazepine IV.

Scheme 2

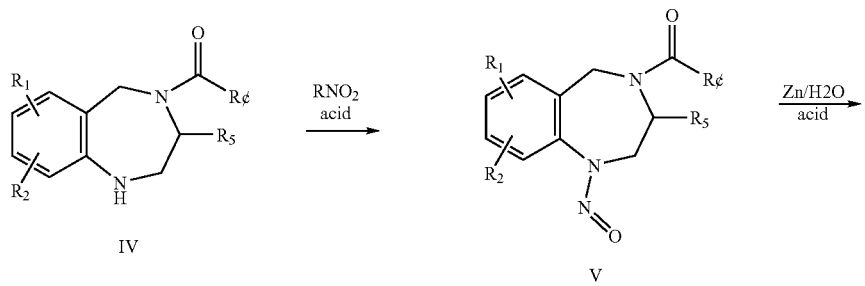

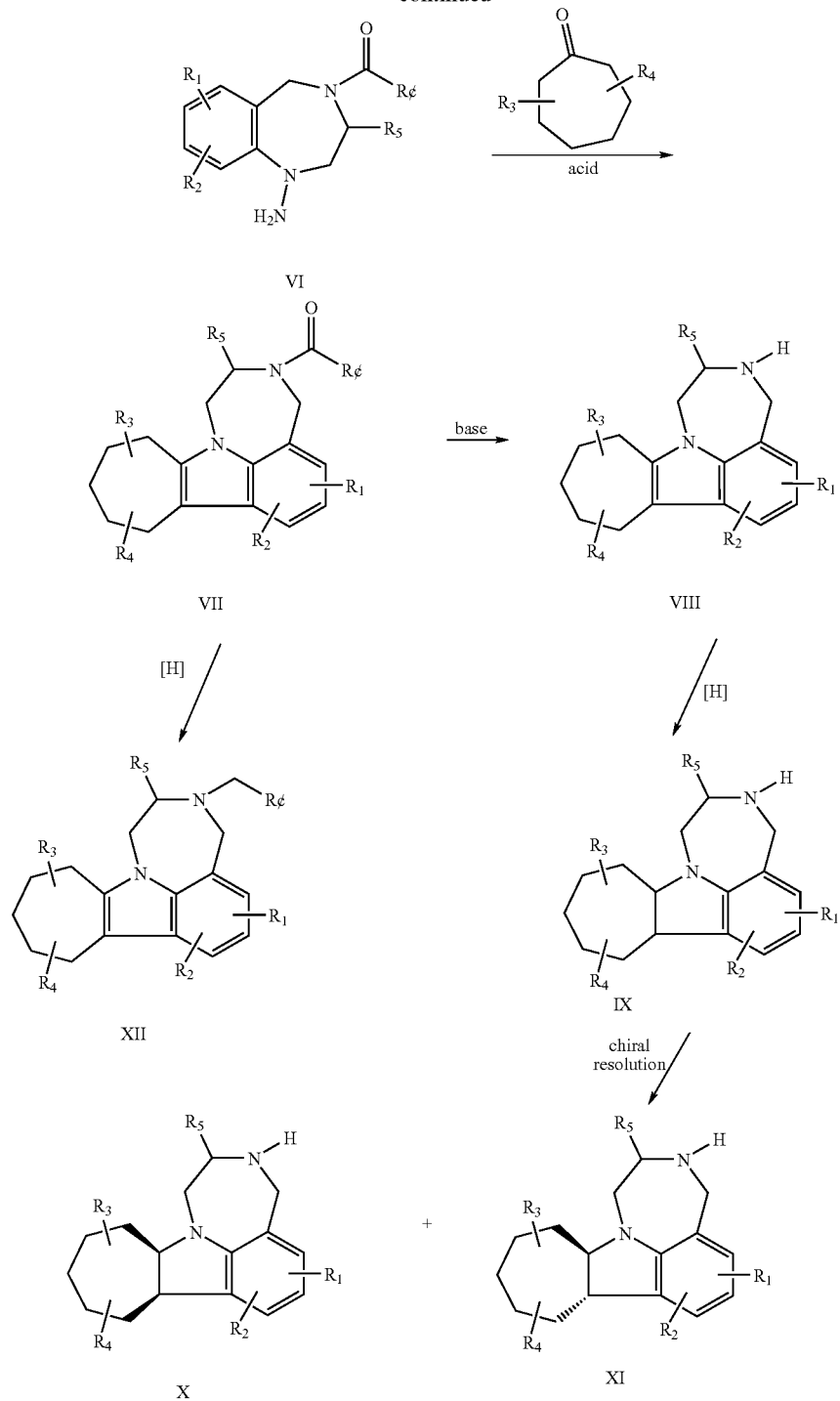

According to Scheme 2, Intermediate IV is allowed to react with a nitrosating agent, such as sodium nitrite, in the presence of an acid, such as acetic acid, to give nitroso compounds V. The nitroso compounds are reduced to hydrazines VI using a reducing agent, such as zinc powder in acetic acid and water. The hydrazines VI are allowed to react with substituted or unsubstituted cycloheptanones in acid, such as acetic acid, to give the fused indoles VII. The fused indoles VII can be treated with a base, such as NaOH, in a polar solvent, such as water or an alcohol, or with an acid, such as hydrochloric acid, to give the fused indoles VIII, which are products of this invention. In addition, fused indoles VII can be reduced, with a reducing agent, such as sodium cyanoborohydride, in the presence of an acid, such as acetic acid, to give fused indolines IX which are products of this invention. Fused indolines IX are diastereoisomeric mixtures that can be resolved using chiral HPLC or chiral resolving agents to give stereo isomers X and XI and enantiomers thereof, which are products of this invention. Also, compounds VII can be reduced with reducing agents, such as a borane-THF complex, to give XII which are compounds of this invention.

The acylation steps of this invention are understood to include reactions of the appropriate compound with any acylating agent and reaction conditions known in the art. Useful in these steps are acylating agents include acid halides and esters or anhyrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

The ability of the compounds of this invention to act as $5HT_{2C}$ agonists was demonstrated in several standard pharmacological test procedures; the procedures used and results obtained are provided below.

Test Procedures $5HT_{2C}$ Receptor Binding Test Procedure

To evaluate high affinity for the $5HT2_C$ receptor, a CHO (Chinese Hamster Ovary) cell line transfected with the cDNA expressing the human 5-hydroxytryptamine$2_C$ (h5HT$2_C$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10-25 microliter (μl) volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1-2 mg per ml of suspension. The preparation membrane suspension (many times concentrated) was aliquoted in 1 ml volumes and stored at −70 C until used in subsequent binding experiments.

Binding measurements were performed in a 96 well microtiter plate format, in a total volume of 200 μl. To each well was added: 60 μl of incubation buffer made in 50 mM Tris.HCl buffer, pH 7.4 and containing 4 mM $CaCl_2$; 20 μl of [$^{125}$I] DOI (S.A., 2200 Ci/mmol, NEN Life Science).

The dissociation constant, KD of [$^{125}$I] DOI at the human serotonin $5HT_{2C}$ receptor was 0.4 nM by saturation binding with increasing concentrations of [$^{125}$I] DOI. The reaction was initiated by the final addition of 100.0 μl of tissue suspension containing 50 μg of receptor protein. Nonspecific binding is measured in the presence of 1 μM unlabeled DOI added in 20.0 μl volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 μl Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs log concentration of test drug. Non linear regression analysis of data points yields both the IC50 and the Ki values of test compounds with 95% confidence limits. Alternatively, a linear regression line of decline of data points is plotted, from which the IC50 value can be read off the curve and the Ki value determined by solving the following equation:

$$Ki = \frac{IC50}{1 + L/KD}$$

where L is the concentration of the radioactive ligand used and the KD is the dissociation constant of the ligand for the receptor, both expressed in nM.

The following Ki's are provided for various refrence compounds:

Ki value and 95% confidence interval.

| | |
|---|---|
| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |
| mCPP | 6.5 (4.8–9.0) nM |
| DOI | 6.2 (4.9–8.0) nM |

Stimulation of [$^3$H] Inositol Monophosphate Production by 5-HT$_{2C}$ Agonists.

CHO cells transfected with the cDNA expressing the human 5-HT$_{2C}$ receptor were cultured in Dulbecco's modified Eagle's medium (DMEM) supplemented with 10% fetal bovine serum and non-essential amino acids. Upon reaching confluence the cells were harvested using PBS/EDTA and plated in 24 well plates at an initial density of $2.5 \times 10^5$ cells per well. One (1) ml of maintenance medium containing 1 µCi/ml myo-[$^3$H] inositol was added to each well. After 48 hours labeling, the cells were washed once with 0.5 ml DMEM containing 25 mM HEPES and 10 mM LiCl, then preincubated with the medium for 30 min (antagonists were included in this period if tested). At the end of the preincubation, the medium was removed, the cells were then incubated with test compounds (in presence of antagonists if needed) for 30 min. The reaction was terminated by removal of the incubation solution and addition of 0.5 ml ice-cold 5% PCA, followed by 15 to 30 min incubation on ice. 200 µl of 0.5 M Tes/1.5 M $K_2CO_3$ was added to each well to neutralize to pH 7, and plates were left on ice for another 15 to 30 min to precipitate all salts. The liquid and solid phases were separated by centrifugation.

A portion (350 µl) of the upper aqueous phase was applied to Dowex AG-1X8 (formate form, 100-200 mesh) columns. The columns were then washed stepwise with 10 ml of water and 10 ml of 25 mM ammonium formate to remove free myo-[$^3$H]inositol and deacylated phosphoinositol, respectively. Finally 10 ml of 0.2 M ammonium formate solution was applied to the columns to elute [$^3$H] inositol monophosphate ([$^3$H] $IP_1$) directly into scintillation vials. Of this eluate, 1 ml was used to determine radioactivity by scintillation counting.

Agonist-stimulated levels of [$^3$H]inositol monophosphate ($IP_1$) is expressed as a percentage of the response observed with a maximally effective concentration of 5-HT (10 µM). A 3-parameter logistic function is used to generate estimate of $EC_{50}/IC_{50}$. Antagonists are tested in the presence of 10 µM 5-HT.

The following data are provided for various reference compounds:

| | | |
|---|---|---|
| 5-HT | 15.1 nM | $EC_{50}$ |
| mCPP | 46.8 nM | $EC_{50}$ |
| | 60% | $E_{MAX}$ (relative to 5-HT) |
| SB200646 | 286 nM | $IC_{50}$ (10 µM 5-HT as agonist) |

Results

| | Results from in vitro Test Procedures | | |
|---|---|---|---|
| Compound | $5HT_{2C}$ Affinity DOI/Agonist binding (Ki, nM) | $5HT_{2C}$ % Emax (5HT, 100%) | Stimulation of IP3 (EC50, nM) |
| Example 1 | 38 | 73 | 500 |
| Example 2 | | | |

The results obtained in this standard pharmacological test procedures demonstrate that the compounds of this invention are $5HT_{2C}$ receptor agonists useful for the treatment of diseases involving the central nervous system such as obsessive-compulsive disorder; depression; anxiety; generalized anxiety disorder, panic disorder; schizophrenia; migraine; sleep disorders, such as sleep apnea; eating disorders, such as hyperphagia; obesity; epilepsy, and spinal cord injury.

This invention also comprises pharmaceutical compositions comprising one or more of the compounds of this invention, or a pharmaceutically acceptable salt thereof, and one or more pharmaceutically acceptable carriers or excipients. The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

As used herein, the terms "pharmaceutically effective amount" or "therapeutically effective amount" means the total amount of each active component of the pharmaceutical composition or method that is sufficient to show a meaningful patient benefit, i.e., treatment, prevention or amelioration of the cause or symptoms of the malady or condition, or an increase in rate of treatment, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The dosage requirements vary with the particular compositions employed, the route of administration, the severity of the symptoms presented and the particular subject being treated. Based on the results obtained in the standard pharmacological test procedures, projected daily dosages of active compound would be 0.02 μg/kg-750 μg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following exemplifies the preparation of compounds representative of this invention.

EXAMPLE 1

1,2,3,4,9,10,11,12-Octahydro-8H-cyclohepta[b][1,4]diazepino[6,7,1-hi]indole

Intermediate A. 4-Acetyl-2,3,4,5-tetrahydro-1H-benzodiazepine

Acetic anhydride (0.60 mL) was added dropwise to a stirred suspension of 2,3,4,5-tetrahydro-1H-benzodiazepine (950 mg, 6.4 mmol) in anhydrous ether (25 mL). After refluxing for four hours, the reaction mixture was filtered to remove a solid. Evaporation of the filtrate gave a residue which was purified by chromatography on silica gel eluting with 5% methanol in ethyl acetate. Evaporation of the product fractions gave an oil. The solid removed by filtration above contained a mixture of starting material and product by thin layer chromatography. The solid was partitioned between water and methylene chloride to remove salts and the organic portion was purified on silica gel as described above. Evaporation of the product fractions gave the product as an oil. Both product oils were dried under oil pump vacuum and gradually solidified. The first crop of intermediate A. (322 mg) melted at 83-85° C. (lit. mp: 84-86° C. recrystallized from ether). The second crop of intermediate A (450 mg) isolated from the solid, melted at 75-79° C.

Anal. Calcd. for $C_{11}H_{14}N_2O$. Theory: % C, 69.44; % H, 7.42; % N, 14.73 Found: % C, 69.6; % H, 7.52; % N, 14.71.

Intermediate A (450 mg, 2.36 mmol) was partially dissolved in water (3.8 mL) containing conc. HCl (0.23 mL) while chilling in an ice/water bath. The ice bath was removed and a solution of $NaNO_2$ dissolved in water (0.4 mL) was added dropwise with stirring. A color change from yellow to yellow/brown resulted and an oil separated. The oil was extracted into methylene chloride, dried ($MgSO_4$), filtered and evaporated to give an oil which was dissolved in glacial acetic acid (5.4 mL). Powered zinc (1.16 g, 17.8 mmol, 7.5 eq) was added portionwise at 25-35° C. (exotherm) and the mixture was allowed to stir an additional hour after the addition of zinc was complete. The reaction mixture was filtered into a flask containing cycloheptanone (0.28 g, 2.6 mmol, 1.12 eq) and was heated at 100° C. for 1.5 h. The acetic acid was removed by evaporation under reduced pressure and the residue was purified by column chromatography on silica gel eluting with 3% methanol in methylene chloride to give a residue. The residue was dissolved in conc. HCl (10 mL) and heated under reflux for 5 h. A precipitate formed. The reaction mixture was cooled and filtered to collect a solid which was recrystallized from water to give the hydrochloride salt of the title compound as a tan solid, mp: 303-306° C.

Anal. Calcd. For $C_{16}H_{20}N_2O \cdot HCl \cdot 0.10\ H_2O$. Theory: % C, 69.98; % H, 7.67; % N, 10.10. Found: % C, 68.95; % H, 7.55; % N, 10.05.

EXAMPLE 2

1,2,3,4,8,9,10,11,12,12a-Decahydro-7bH-cyclohepta[b][1,4]diazepino[6,7,1-hi]indole The product of Example 1 (223 mg, 0.8 mmol) was dissolved in glacial acetic acid with stirring and the solution was cooled in an ice/water bath. Solid sodium cyanoborohydride (75 mg) was added portionwise with stirring. The ice bath was removed and the reaction mixture was allowed to stir at room temperature under a nitrogen atmosphere for 3 h. The volatiles were removed under reduced pressure to give a colorless oil which was partitioned between 2.5 N NaOH and ethyl acetate. The organic phase was washed with saturated NaCl solution, then water and dried ($MgSO_4$). The dried solution was filtered and the filtrate was evaporated under reduced pressure to give a pale yellow oil (206 mg).

The oil (196 mg) was treated with a solution of KOH (412 mg) dissolved in water (1 mL) and methanol (2 mL) and heated in an oil bath (95° C.) for 25 h. The volatiles were removed under reduced pressure to give a clear oil (120 mg). The oil was dissolved in 2-propanol and treated with an excess of ethereal HCl to give the hydrochloride salt of the title compound as a yellow solid (119 mg), mp: 258-263° C. (recrystallized from 2-propanol).

Anal. Calcd for $C_{16}H_{22}N_2 \cdot HCl \cdot 0.25\ H_2O$. Calcd: % C, 67.83; % H, 8.36; % N, 9.89. Found: % C, 67.81; % H, 8.01; % N, 9.50.

What is claimed is:

1. A method of treating in a mammal a condition selected from at least one of schizophrenia, bipolar disorders, or psychosis, the method comprising administering to a mammal a pharmaceutically effective amount of a compound of formula I or a pharmaceutically acceptable salt thereof:

13

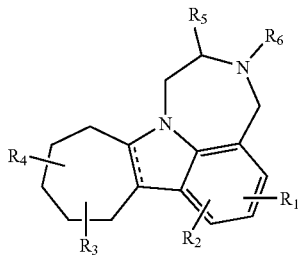

wherein:
R₁ and R₂ are each, independently, hydrogen, alkyl of 1-6 carbon atoms, cycloalkyl of 3 to 7 carbon atoms, —CH₂-cycloalkyl of 3 to 7 carbon atoms, alkoxy of 1-6 carbon atoms, halogen, fluorinated alkyl of 1 to 6 carbon atoms, —CN, —NH—SO₂-alkyl of 1-6 carbon atoms, —SO₂—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, phenoyl or thiophenoyl;
R₃ and R₄ are each, independently, hydrogen, C₁-C₆ alkyl or cycloalkyl of 3 to 7 carbon atoms;
R₅ is hydrogen or C₁-C₆ alkyl;
R₆ is hydrogen or C₁-C₆ alkyl; and
wherein the dashed line indicates an optional double bond.

2. The method of claim 1 wherein the mammal is a human.

3. The method of claim 2 wherein R₁, R₂, R₃, R₄, R₅, and R₆ are independently selected from H or alkyl of 1-6 carbon atoms, or a pharmaceutically acceptable salt thereof.

4. The method of claim 2 wherein the compound administered is selected from at least one of 1,2,3,4,9,10,11,12-octahydro-8H-cyclohepta[b][1,4]diazepino[6,7,1-hi]indole; or 1,2,3,4,8,9,10,11,12,12a-decahydro-7bH-cyclohepta[b][1,4]diazepino[6,7,1-hi]indole; or a pharmaceutically acceptable salt thereof.

5. The method of claim 2 wherein the condition is schizophrenia.

6. A method of treating in a mammal a condition selected from drug or alcohol addiction, social phobias, panic disorder, sexual dysfunction, sleep disorders, eating disorders, gastrointestinal disorders, diabetes, obesity, epilepsy, or premenstrual tension, the method comprising administering to a mammal a pharmaceutically effective amount of a compound of formula I or a pharmaceutically acceptable salt thereof:

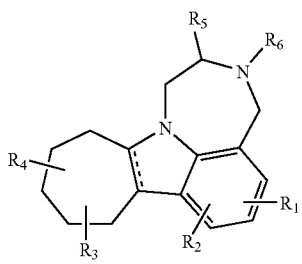

wherein:
R₁ and R₂ are each, independently, hydrogen, alkyl of 1-6 carbon atoms, cycloalkyl of 3 to 7 carbon atoms,

14

—CH₂-cycloalkyl of 3 to 7 carbon atoms, alkoxy of 1-6 carbon atoms, halogen, fluorinated alkyl of 1 to 6 carbon atoms, —CN, —NH—SO₂-alkyl of 1-6 carbon atoms, —SO₂—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, phenoyl or thiophenoyl;
R₃ and R₄ are each, independently, hydrogen, C₁-C₆ alkyl or cycloalkyl of 3 to 7 carbon atoms;
R₅ is hydrogen or C₁-C₆ alkyl;
R₆ is hydrogen or C₁-C₆ alkyl; and
wherein the dashed line indicates an optional double bond.

7. The method of claim 6 wherein the mammal is a human.

8. The method of claim 7 wherein the condition is selected from diabetes or obesity.

9. The method of claim 7 wherein the condition is selected from epilepsy.

10. The method of claim 7 wherein the condition is selected from sexual dysfunction.

11. The method of claim 7 wherein R₁, R₂, R₃, R₄, R₅, and R₆ are independently selected from H or alkyl of 1-6 carbon atoms, or a pharmaceutically acceptable salt thereof.

12. The method of claim 7 wherein the compound administered is selected from at least one of 1,2,3,4,9,10,11,12-octahydro-8H-cyclohepta[b][1,4]diazepino[6,7,1-hi]indole; or 1,2,3,4,8,9,10,11,12,12a-decahydro-7bH-cyclohepta[b][1,4]diazepino[6,7,1-hi]indole; or a pharmaceutically acceptable salt thereof.

13. A method of treating a mammal suffering from stroke, trauma or a spinal cord injury, the method comprising administering to a mammal a pharmaceutically effective amount of a compound of formula I or a pharmaceutically acceptable salt thereof:

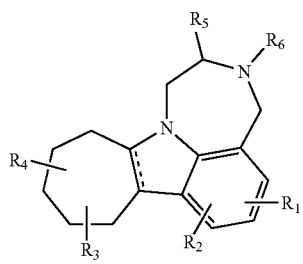

wherein:
R₁ and R₂ are each, independently, hydrogen, alkyl of 1-6 carbon atoms, cycloalkyl of 3 to 7 carbon atoms, —CH₂-cycloalkyl of 3 to 7 carbon atoms, alkoxy of 1-6 carbon atoms, halogen, fluorinated alkyl of 1 to 6 carbon atoms, —CN, —NH—SO₂-alkyl of 1-6 carbon atoms, —SO₂—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, phenoyl or thiophenoyl;
R₃ and R₄ are each, independently, hydrogen, C₁-C₆ alkyl or cycloalkyl of 3 to 7 carbon atoms;
R₅ is hydrogen or C₁-C₆ alkyl;
R₆ is hydrogen or C₁-C₆ alkyl; and
wherein the dashed line indicates an optional double bond.

14. The method of claim 13 wherein the mammal is a human.

15. The method of claim 14 wherein $R_1$, $R_2$, $R_3$, $R_4$, $R_5$, and $R_6$ are independently selected from H or alkyl of 1-6 carbon atoms, or a pharmaceutically acceptable salt thereof.

16. The method of claim 14 wherein the compound administered is selected from at least one of 1,2,3,4,9,10,11,12-octahydro-8H-cyclohepta[b][1,4]diazepino[6,7,1-hi]indole; or 1,2,3,4,8,9,10,11,12,12a-decahydro-7bH-cyclohepta[b][1,4]diazepino[6,7,1-hi]indole; or a pharmaceutically acceptable salt thereof.

* * * * *